United States Patent [19]
Miller

[11] Patent Number: 6,165,138
[45] Date of Patent: *Dec. 26, 2000

[54] SELF-SEALING CLOSURE FOR A MEDICAL SPECIMAN COLLECTION CONTAINER

[75] Inventor: Henry F. Miller, Clifton, N.J.

[73] Assignee: Becton Dickinson and Company, Franklin Lakes, N.J.

[*] Notice: This patent issued on a continued prosecution application filed under 37 CFR 1.53(d), and is subject to the twenty year patent term provisions of 35 U.S.C. 154(a)(2).

[21] Appl. No.: 09/163,868

[22] Filed: Sep. 30, 1998

[51] Int. Cl.[7] .......................................................... A61B 5/00

[52] U.S. Cl. ............................................. 600/577; 604/167

[58] Field of Search ..................................... 600/573, 577; 604/256, 167

[56] References Cited

U.S. PATENT DOCUMENTS

| | | | |
|---|---|---|---|
| 3,974,928 | 8/1976 | Domaracki et al. | 215/211 |
| 4,087,016 | 5/1978 | Touns et al. | 215/211 |
| 4,397,706 | 8/1983 | Allen et al. | 156/242 |
| 5,433,716 | 7/1995 | Leopardi et al. | 604/415 |
| 5,520,655 | 5/1996 | Davila et al. | 604/256 |

*Primary Examiner*—Max Hindenburg
*Assistant Examiner*—Pamela Wingood
*Attorney, Agent, or Firm*—Nanette S. Thomas, Esq.

[57] ABSTRACT

A blood collection tube is provided having a sealingly engaged elastomeric disk bonded over the open end of the tube. The disk has two opposing major surfaces and is bonded to the tube while deformed in a generally arcuate configuration. One of the major surface faces exteriorly from the tube and the other major surface faces interiorly into the tube. The exterior-facing major surface of the disk is placed in tension and the interior-facing major surface is placed in compression.

2 Claims, 10 Drawing Sheets

SELF-SEALING CLOSURE FOR A MEDICAL SPECIMAN COLLECTION CONTAINER

BACKGROUND OF THE INVENTION

1. Field of the Invention

The present invention relates to a closure device for medical specimen collection containers and more specifically, to an improved closure disk for effecting reseal in punctured blood collection tubes.

2. Description of Related Art

Blood samples and other medical specimens are routinely taken and collected in a specimen collection container. With blood samples, the container is typically in the shape of a hollow tube with one end closed by a semi-spherical portion and the other end open. The open end is sealable by a cover. The tube thus defines an interior chamber for collecting and holding the blood sample.

Blood collection tubes can be formed with a vacuum chamber allowing the interior of the container to be at zero or lower-than-ambient pressure. It is well known that such a vacuum facilitates the drawing of blood from a body. Once the cover is punctured by a probe or needle drawing a medical sample, the vacuum will be released.

The cover is typically made of an impervious elastomeric material which is penetrable by a hollow probe or needle through which the blood sample is delivered to or removed from the chamber. Friction between the elastomeric cover material surrounding the needle and the needle surface performs a wiping function that wipes blood from the exterior surface of the needle as the needle is withdrawn from the chamber. The elastomeric cover also tends to reseal the hole produced by the needle to prevent leakage after the needle is withdrawn from the cover. The cover is typically held in place by either an interference fit between the tube and the cover or by adhesively affixing the cover to the open end of the tube.

Even though the cover material is sufficiently elastomeric so as to close in on itself and seal the probe opening to a certain extent when the probe is removed, the hole though which the probe is withdrawn has the potential to permit blood leakage in the event that the tube is mishandled or otherwise comes to rest in an inverted or non-upright position. Multiple punctures in the cover will compound this problem. In some instances a single needle will penetrate and withdraw from several tubes such as during the taking of multiple blood samples from a single patient. In these instances it is important that the probe be thoroughly wiped as it is withdrawn from each tube. This prevents the probe from depositing some non-wiped sample on the exterior surface of any subsequently-punctured covers and also prevents exposure of a non-wiped needle to the phlebotomist. Similarly, the cover of a single tube may be penetrated several times during the course of taking a blood sample and subsequently removing all or some of the blood sample for analysis. In these cases it is important that cover be able to continue to reseal so that cover integrity is maintained.

The cover performs a critical safety role in that it must ensure that the sample taken does not in some way escape the tube by either adhering to the needle or by leaking out the opening the probe creates after penetrating the cover. Therefore the cover should adequately reseal the opening and wipe the needle clean as it withdraws so that no sample is exposed to the phlebotomist or the health care worker directly from the needle or by the leakage through the opening created by the needle puncture.

As the safety of the health care workers and the preservation of the samples are of paramount interest, it is therefore desirable to provide a closure for a medical specimen collection container that provides higher safety through improved reseal and wiping characteristics.

SUMMARY OF THE INVENTION

The present invention is an improved closure for a medical specimen collection container and a method of sealing a medical specimen collection container tube with a closure device having improved resealing characteristics.

Preferably, the present invention is a method for sealing a medical specimen collection container tube that will result in an overall reduction in the cost required to produce a closure which provides adequate shelf life, withstands shipment stresses, and reseals satisfactorily after puncture.

Preferably, the present invention comprises a closure for a medical specimen collection container. The closure includes a impervious elastomeric generally disk-shaped member having two opposing major surfaces. The disk-shaped member is deformed in a generally arcuate configuration so as to place one of said major surfaces in tension and the opposing major surface in compression.

Preferably, the present invention comprises a closure for a blood collection tube wherein a closure disk having two opposing major surfaces is deformed by a bending moment at its outer circumference. The bending moment induces deformation of the closure disk into a generally arcuate configuration having one major surface in tension and the opposing major surface in compression. The bending moment may be applied by adhering the closure disk to a beveled rim having a curvature which is imparted to the disk.

Furthermore, the elastomeric closure disk may include a gas barrier adhered to the major surface placed in compression. When the tube and closure of the present invention are mated, the major surface in compression is thereby disposed adjacent the interior of the container and the major surface in tension is thereby disposed adjacent the exterior of the container. The radial compression forces of the interior surface will thereby provide improved wiping of a withdrawing probe and improved resealing characteristics for the closure disk.

DETAILED DESCRIPTION

The present invention is preferably a medical specimen collection container including an improved closure. More preferably, the present invention is a closure for a blood collection tube.

Figure 1:
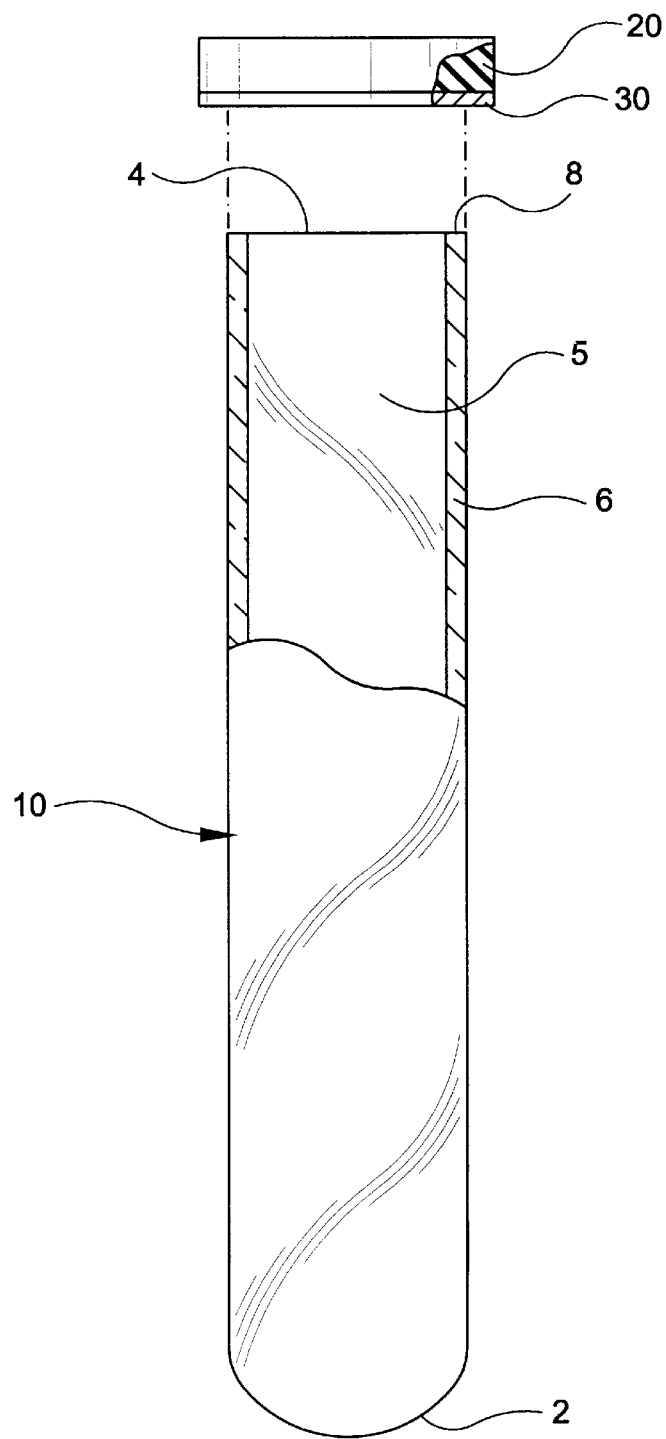
FIG. 1 shows the components of a standard vacuum tube for collecting blood samples.

Referring to FIG. 1, a standard blood collection tube 10 for collecting blood samples is shown. Tube 10 includes an elongate cylindrical wall 6 and has a closed lower end 2, an open upper end 4, and a generally flat rim 8 around the open end. Tube 10 defines an interior 5 for accumulating the blood sample. Tube 10 may be formed of conventional materials traditionally used for such purposes. Tube 10 may be preferably formed of a rigid transparent material such as glass. However, other materials such as polymers may also be employed.

Figure 3:
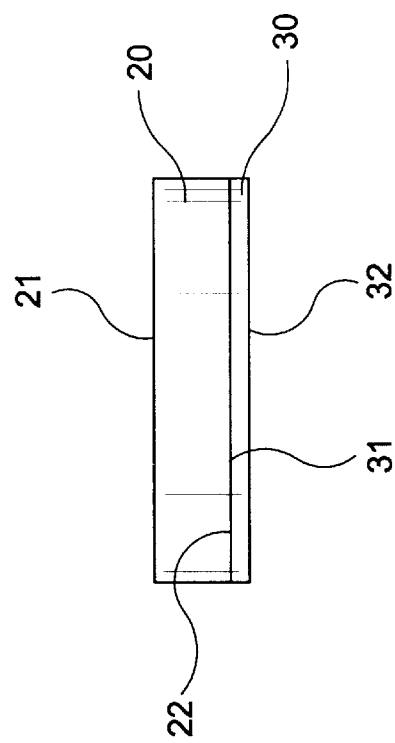
FIG. 3 shows a side view of a typical elastomeric cover disk including an attached gas barrier.
Figure 2:
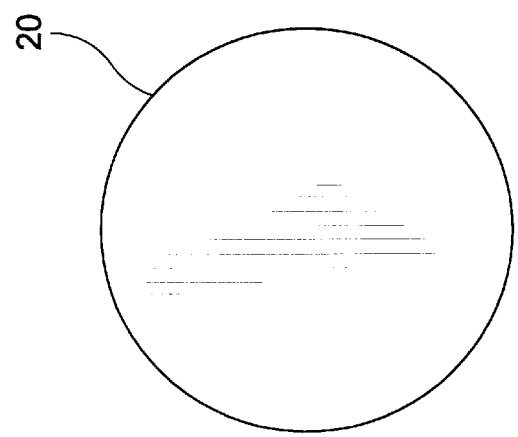
FIG. 2 shows a top view of a typical elastomeric cover disk used with a standard vacuum tube.

Blood collection tube 10 typically employs a cover over the open end 4. The cover may take the form of an elastomeric disk 20. As shown in further detail with additional reference to FIGS. 2 and 3, disk 20 is generally round and planar in shape having two opposing major surfaces 21 and 22 and a circumferential edge 1. Disk 20 is sized to fit over flat rim 8 so as to completely cover open end 4. Disk 20 is typically fabricated from an elastomeric material to effect wiping and resealing characteristics when punctured by a blood collection needle. Disk 20 may also have disposed on major surface 22 a gas barrier 30. Barrier 30 includes opposing major surfaces 31 and 32 with major surface 31 adhered to major surface 22. Barrier 30 may be formed of a sheet of material exhibiting sufficient gas impermeability and in the preferred embodiment is formed of a metallic foil such as 0.0005"-thick aluminum or the like.

Figure 5:
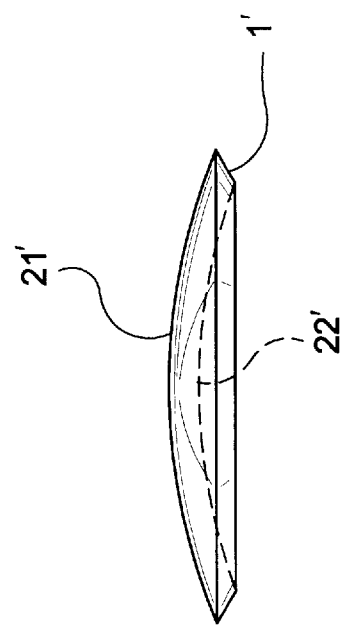
FIG. 5 is a side view of the closure disk of FIG. 4.
Figure 4:
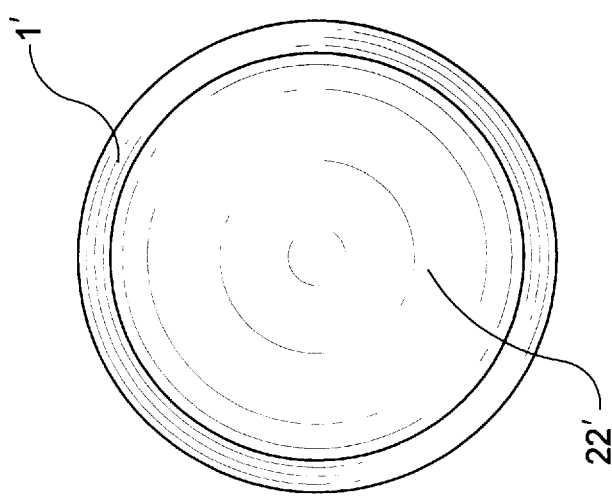
FIG. 4 is a bottom view of a closure disk deformed in accordance with the present invention.
Figure 6:
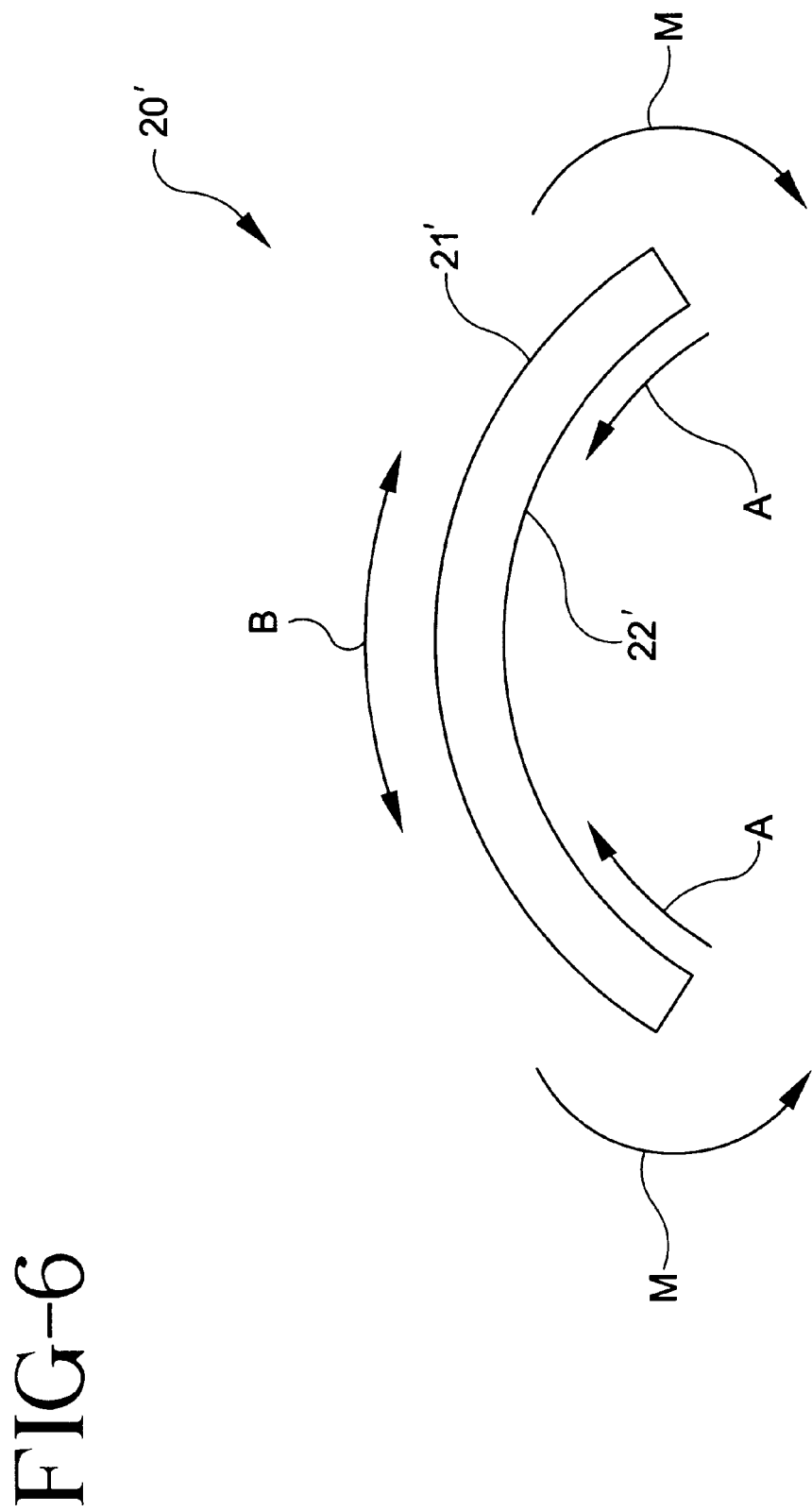
FIG. 6 illustrates the reaction of a portion of a closure disk to a bending moment applied in accordance with the present invention, accentuating the relative tension and compression induced in the major surfaces thereof.

The present invention, seeking to improve the wiping and resealing characteristics of the cover, contemplates providing an elastomeric member for closing a blood collection tube by putting disk 20 in a state of tension and compression. FIGS. 4, 5, and 6 illustrate the present invention. It is contemplated that by deforming disk 20 into a disk 20' having a generally arcuate configuration, improved resealing properties will be imparted thereto.

FIGS. 4 and 5 show bottom and side views, respectively, of the closure disk 20' of the present invention after its deformation by bending disk 20 into an arcuate configuration. Like reference numerals will be used to denote like components. Major surface 21', forming the exterior surface of disk 20', is deformed into a convex condition while major surface 22', forming the interior surface of disk 20' is deformed into a concave condition. FIG. 6 shows a schematic representation of a cross-section of closure disk 20' and demonstrates the effect of a bending moment applied in the direction of M about the edge 1'. Arrow A indicates that interior surface 22' of disk 20' is subjected to a radial compression force because it has now been deformed to cover a smaller surface area. Arrow B, on the other hand, indicates that exterior surface 21' is placed in a state of radial tension as it has now been deformed in on itself to provide a larger surface area. The compression forces represented by arrow A along interior surface 22' provide greater frictional forces for wiping blood from the withdrawing needle and a higher resealing force once the probe is withdrawn. In accordance with the present invention, disk 20' is, therefore, generally flexible and may be fabricated from any material deformable in accordance with the present invention. Preferably, disk 20' is made from an elastomeric material such as rubber, TPE, thermoplastic, plastic foam, or the like.

Figure 7:
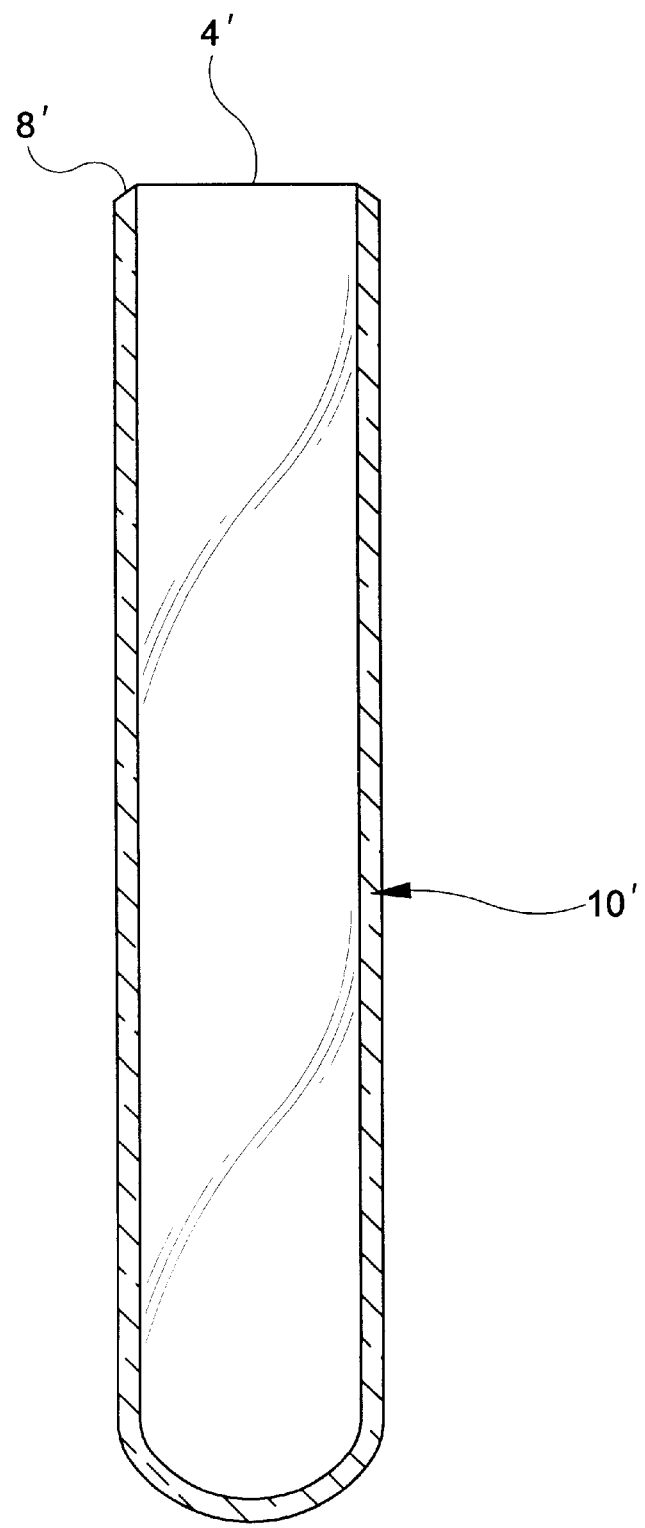
FIG. 7 is a cross-sectional view of a test tube with a beveled rim for imparting a bending moment to the closure disk of the present invention.
Figure 8:
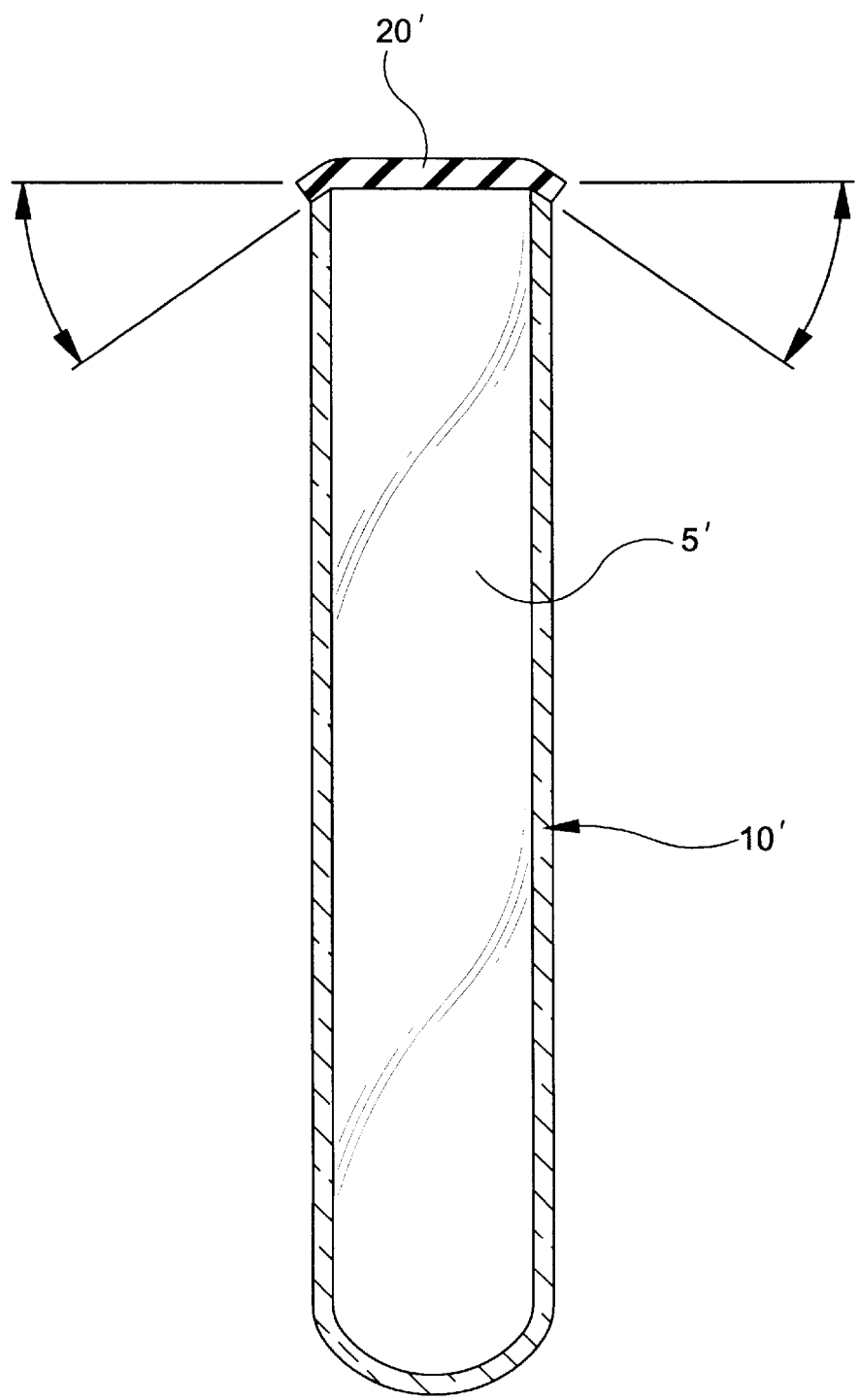
FIG. 8 is a cross-sectional view of the test tube of FIG. 7 including the closure disk disposed thereover.
Figure 11:
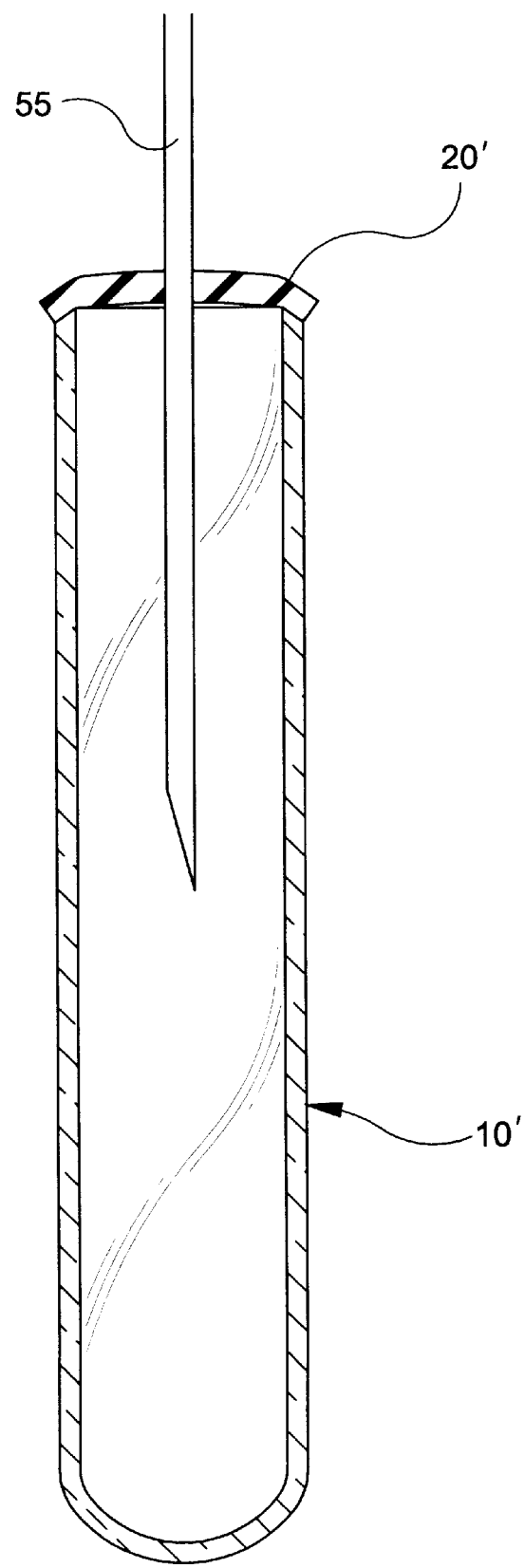
FIG. 11 shows a cross-sectional view of the closure disk of the present invention adhered to a vacuum tube with a needle penetrating therethrough.
Figure 12:
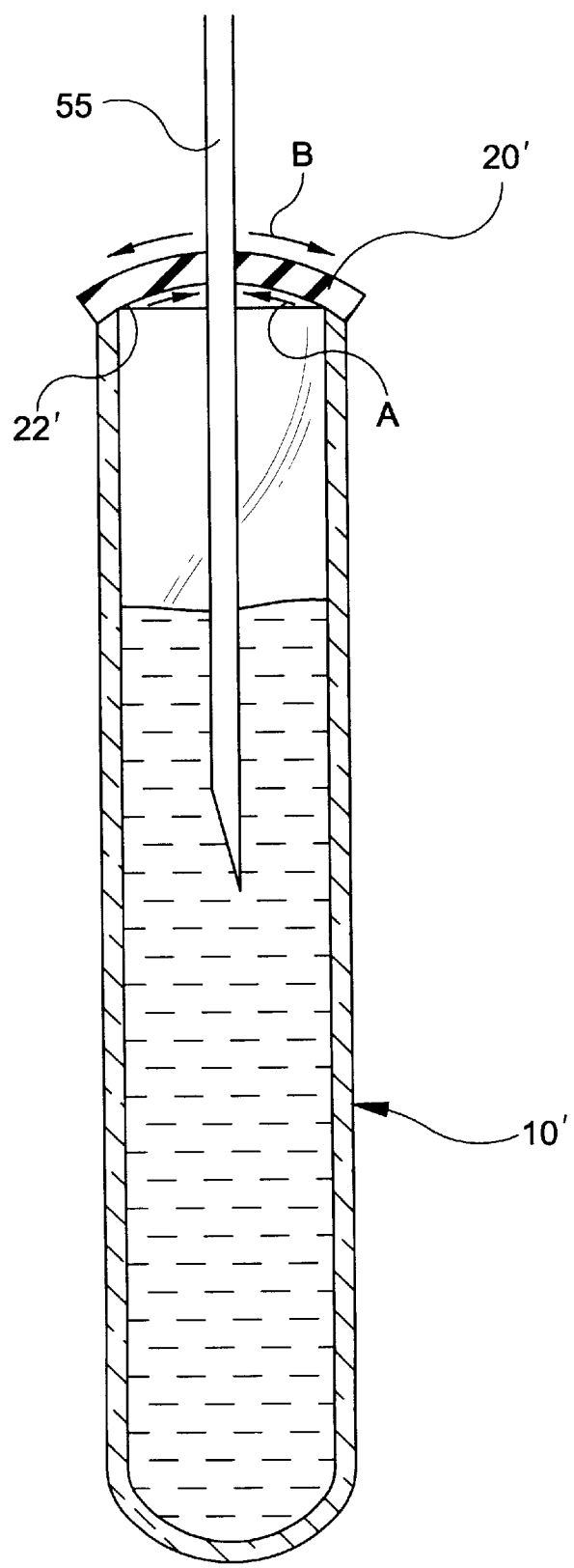
FIG. 12 shows a cross-sectional view of the closure disk of the present invention adhered to a tube after the vacuum has been released by the needle penetrating therethrough and the increased radial forces exerted by the closure disk on the needle.

The preferred method of imparting a bending moment in the direction of arrow M is illustrated in FIGS. 7 and 8. The present invention contemplates producing a blood collection tube 10' to include a beveled rim 8' at the open upper end 4' thereof. Beveled rim 8' is formed by chamfering or tapering the upper end of tube 10' so that the rim 8' bevels downwardly in an outward direction. When the blood collection tube 10' is formed having a vacuum, the disk 20' may be drawn slightly in towards the interior 5' of tube 10', giving the closure a flatter shape as shown in FIG. 11. However, when the closure disk 20' is punctured by a probe 55 during the specimen draw, as shown in FIG. 12, the vacuum is released and disk 20' will assume the configuration shown. The closure disk 20' imparts the higher compression forces at the interior surface 22', as represented by arrows A in FIG. 12, taught by the present invention. Since the interior surface 22' is in radial compression, punctures made by probe 55 and subsequent probes used in specimen analysis will be automatically sealed. In addition, the needle will be wiped of blood during withdrawal from closure disk 20'. As contemplated and described herein, the present invention may be used with a blood collection assembly of the prior art without any additional procedures for, or otherwise inconveniencing, the phlebotomist.

Figure 9:
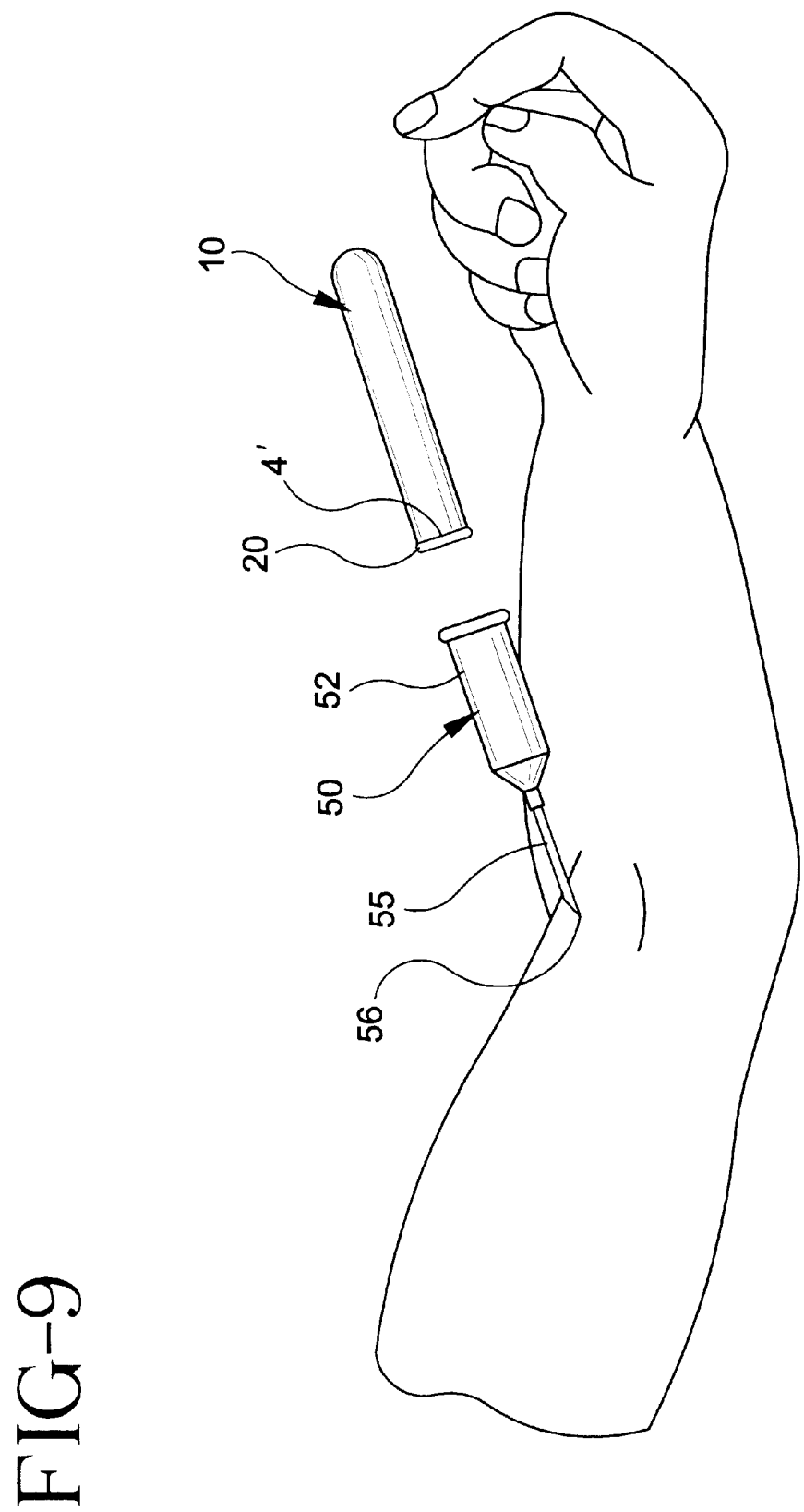
FIG. 9 shows the standard vacuum tube being inserted to a holder for drawing a blood sample.
Figure 10:
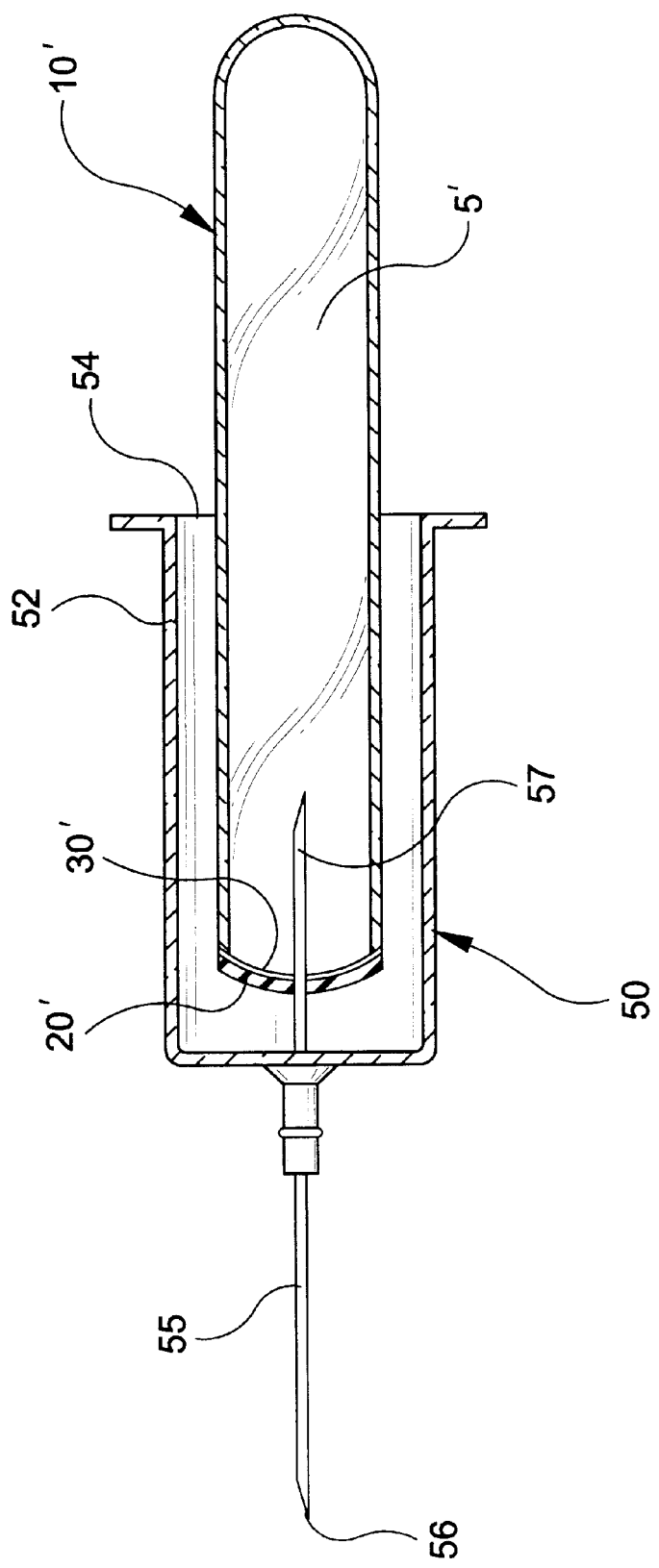
FIG. 10 shows a vacuum tube with a closure disk of the present invention positioned within a holder device.

With reference to FIGS. 9 and 10, the operation of the present invention is described for use in blood collection procedures. FIG. 9 shows that the covered open end 4' of a sample collection tube 10' is inserted into the open end of a holder device 50. FIG. 10 shows that holder device 50 is a conventional member having a cylindrical body 52 supporting needle 55 in one closed end thereof. The needle, having a blood extraction end 56 and a blood expelling end 57, may be a suitable blood collection needle designed for percutaneous insertion into the blood circulation system of a patient by blood extracting end 56. The tube 10' is inserted into the open end 54 of holder 50 so that blood expelling end 57 of needle 55 punctures the elastomeric disk 20' and the gas barrier 30' of tube 10' to enter the interior 5' of tube 10'. As tube 10' is generally a vacuum, the low interior pressure inside tube 10' draws blood through needle 55 into tube 10'. When the phlebotomist has collected a sufficient blood sample, tube 10' is extracted from holder 50.

FIG. 12 shows a blood collection tube with the closure disk of the present invention after the vacuum has been released by the blood expelling end 57 of needle 55 puncturing disk 20'. The release of the vacuum allows the disk 20' to assume the arcuate configuration taught by the present invention. Interior surface 22', now in the concave-compressed configuration, exerts a radial force on the surface of needle 55, as represented by arrows A, effecting a wiping action as needle 55 withdraws therethrough. The same radial forces acting upon needle 55 will also tend to effect a resealing of disk 20' after needle 55 is withdrawn.

The present invention is not limited to tubes having a beveled rim. Other methods for imparting the bending moment on the closure are within the contemplation of the present invention. For example, a cover or adaptor may be placed on a conventional tube where the adaptor imparts the desired arcuate configuration to the disk.

Various other modifications to the foregoing disclosed embodiments will now be evident to those skilled in the art. Thus, the particularly described preferred embodiments are intended to be illustrative and not limited thereto. The true scope of the invention is set forth in the following claims.

What is claimed is:

1. A closure for a blood collection tube wherein said tube comprises an open end with a beveled rim at said open end, and a needle may penetrate said closure comprising:

a disk-shaped elastomeric member having opposed major surfaces comprising an outwardly bowed convex exterior surface, an inwardly bowed concave interior surface and an outer circumference, said member being positionable over said open end of said tube and with said beveled rim of said tube and being resealable; whereby said member provides a wiping force to a needle that is being withdrawn from said member; said disk-shaped elastomeric member being deformed by a bending moment at said outer circumference and into an arcuate configuration so as to place one of said major surfaces in tension and the opposed major surface in compression; and a gas impermeable planar sheet on said interior surface of said member.

2. The closure of claim 1, wherein said elastomeric member is deformed into an outwardly bowed convex configuration and wherein said one major surface defines an exterior surface and said opposed major surface defines an interior surface.

* * * * *